United States Patent [19]

Golyakhovsky

[11] Patent Number: 4,532,922
[45] Date of Patent: Aug. 6, 1985

[54] DEVICES AND METHOD FOR CORRECT APPLICATION OF PLASTER DRESSINGS TO TREAT FRACTURES AND DISLOCATIONS

[76] Inventor: Vladimir Golyakhovsky, 165 W. 91st St., New York, N.Y. 10024

[21] Appl. No.: 586,287

[22] Filed: Mar. 5, 1984

[51] Int. Cl.³ ............................................. A61F 5/04
[52] U.S. Cl. .................................................. 128/91 R
[58] Field of Search ................. 128/90, 91 R, 89, 83

[56] References Cited

U.S. PATENT DOCUMENTS

| | | | |
|---|---|---|---|
| 3,826,252 | 7/1974 | Laico | 128/91 R |
| 4,274,166 | 6/1981 | Chambers | 128/90 |
| 4,381,769 | 5/1983 | Prahl | 128/91 R |
| 4,409,972 | 10/1983 | Prahl | 128/91 R |

Primary Examiner—John D. Yasko
Attorney, Agent, or Firm—Henry R. Lerner

[57] ABSTRACT

A device for correctly applying a plaster dressing or cast to treat a fracture or dislocation of a human body segment. The device comprises a split flexible plastic member normally urged into annular shape and having an outwardly extending peripheral edge portion and a skirt portion depending therefrom. This plastic member is adapted to be placed on the body segment with the skirt portion in surrounding relation thereto whereby the outwardly turned peripheral edge portion defines the limit of the plaster cast or dressing. After the cast has been applied to the body segment and has been set, the plaster member is easily removable from under the cast.

8 Claims, 10 Drawing Figures

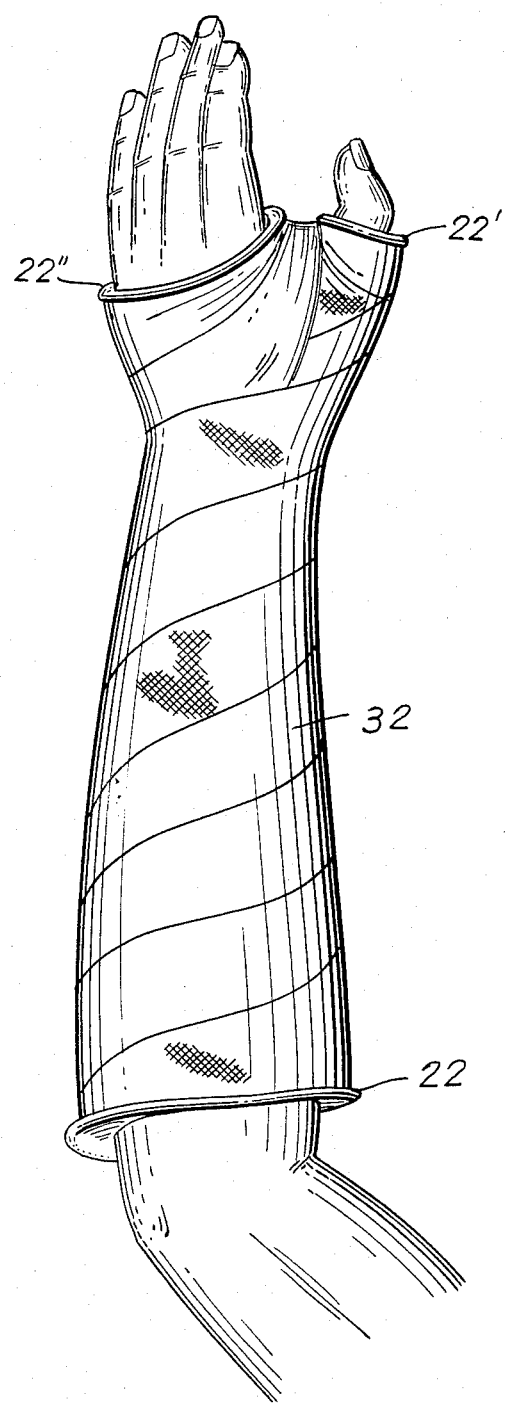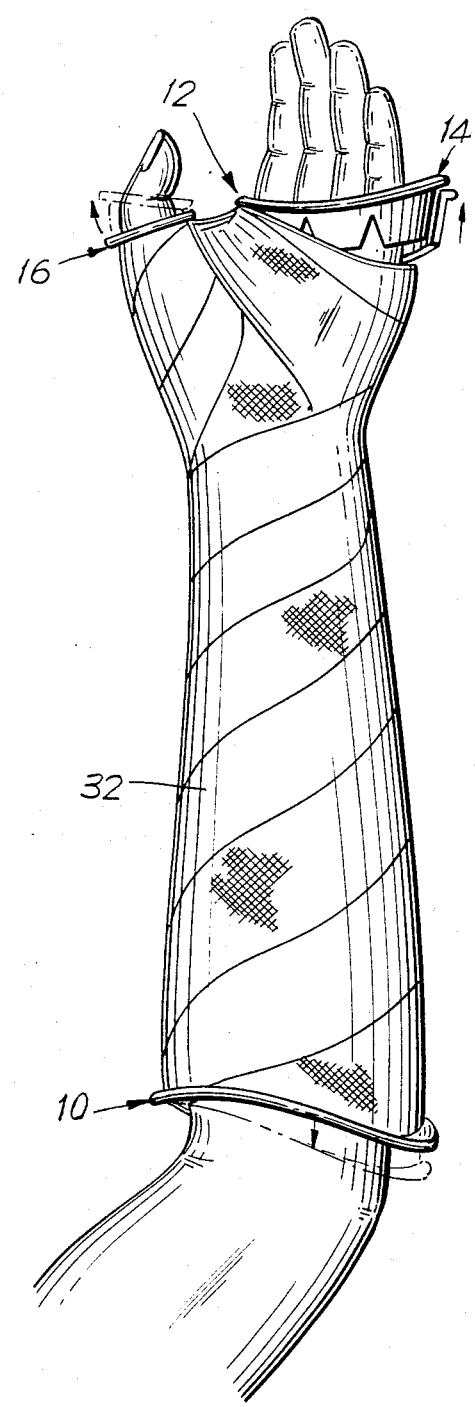

FIG. 6
FIG. 7
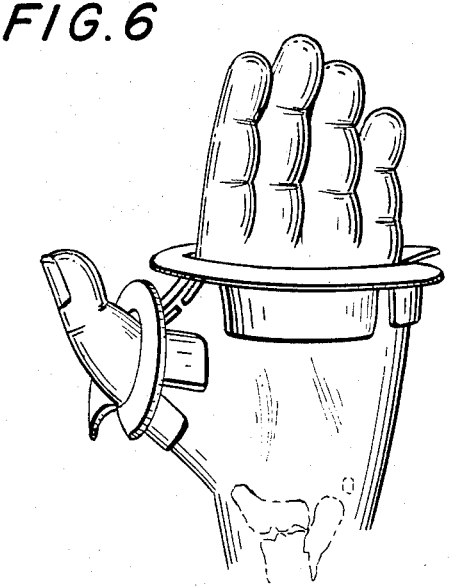
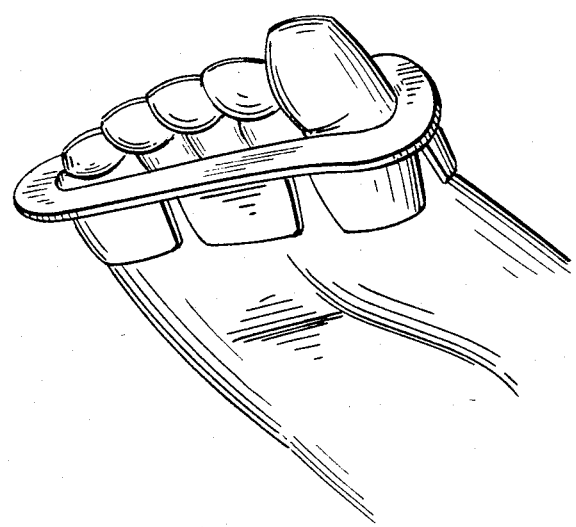
FIG. 8
FIG. 9
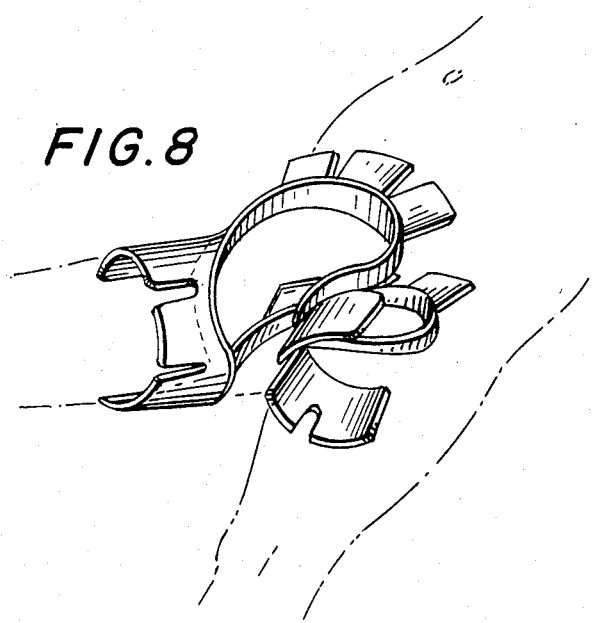
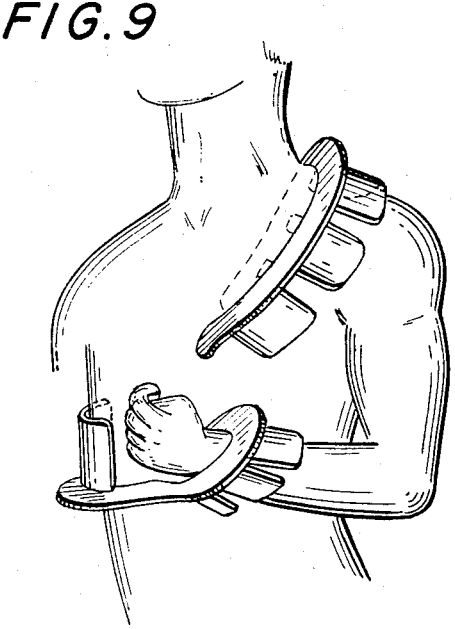
FIG. 10
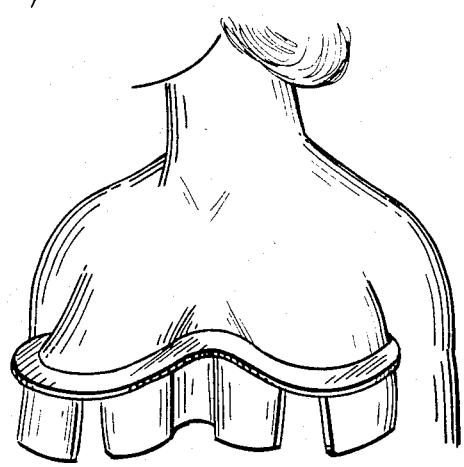

DEVICES AND METHOD FOR CORRECT APPLICATION OF PLASTER DRESSINGS TO TREAT FRACTURES AND DISLOCATIONS

BACKGROUND OF THE INVENTION

The present invention relates to devices for correct application of plaster or cast dressings to treat fractures and dislocations. As used in this application, the term "plaster dressing" is to be construed as synonymous with "plaster cast".

Owing to the plasticity of plaster of Paris, dressings made of this material are indispensible in clinical practice, particularly for treating fresh fractures and dislocations. However, proper application of plaster dressings is a complicated technical procedure calling for a great deal of skill and experience. Such dressings are almost always applied in hospital emergency rooms by young doctors or technicians on duty who rarely possess the skills required to apply dressings properly. Given their lack of experience, most plaster dressings thus applied feature one or more of a range of drawbacks. Sometimes dressing defects are so serious as to give rise to additional complications: skin irritation and lesions, bedsores, pinching of vessels or nerves, contractures stemming from an incorrect position, and many others. Thus, almost half of all dressings must be reapplied or corrected within a few days of the original application, causing further trauma to the injured tissues, creating an additional psychological burden on the patient and adding to the doctor's workload. But even reapplication of a dressing is no sure safeguard against complications, particularly in children and old people. Most of such complications arise as a result of contracture and irritation of soft tissues due to contact with dry plaster at the dressing edges.

Considering that plaster dressings are applied by the millions in all hospitals and that serious complications resulting from application errors run into tens of thousands, there is a great need for an improved technique of plaster dressing application which would represent an important advance from the viewpoint of both medicine and economics.

SUMMARY OF THE INVENTION

In accordance with the invention, there are provided simple, inexpensive and disposable devices to enable correct application of plaster dressings which will prevent typical dressing defects. The dressing devices are of such simplicity that they can be used even by inexperienced physicians and technicians to apply dressings in the best way possible, thus preventing complications.

The devices in accordance with the invention comprise disposable, temporary pads of thin plastic formed in a variety of shapes depending on the application site. All of the dressing devices share four characteristics: (1) Protruding edges bent outward, from 5 mm to 10 mm high, designed to delimit the plaster dressing applied in several turns; (2) Sectional construction, the number of sections depending on the application site; the sections are shaped to conform to the shape of the patient's body segments to be dressed and the sections are interconnected by easily detachable bridge-like links; (3) The protruding edges are split so that the device may be wrapped about the body segment which is involved with the free ends of the edge in overlapping relation, the extent of overlapping being a function of the size and shape of the individual body segment. This permits the device to more closely adhere to the soft tissues without squeezing the latter and also enables the device to be easily removed after the dressing has been applied by simply pulling the free ends of the split edge; for some applications, the free ends do not overlap but are in spaced confronting relation; (4) The bridge-like links are partly split so that they can be easily severed as the device is pulled and removed after the dressing has been applied.

The dressing devices in accordance with the invention are used in the following manner:

Each doctor's office contains a set of dressing devices in a variety of types and sizes. If a plaster dressing is to be applied, the doctor or technician manipulates on the fractured or dislocated segment and then applies to the patient's skin one of the required dressing devices selected individually to fit the segment. The selected device, with the split edge, is easily fit about the body segment with the free ends being in overlapping relation so as to form a continuous cuff-like member having an outwardly extending protruding edge and a skirt depending therefrom. Several turns of common paper pads and then several turns of common plastic bandage are applied about the device, over the skirt, with the outwardly bent peripheral edge defining a limiting guide for the dressing edge, until the dressing is level with the protruding edge of the device. The dressing application technique is the usual one, containing nothing new except for the use of the device designed to guarantee that the dressing is applied properly. When the plaster sets within 10 to 15 minutes, the doctor or technician removes the disposable plastic device by simply pulling it out by the protruding edges. As the pulling force is applied to the device, it separates into several portions under the dressing and smoothly exits without injuring the skin. In some cases, the edges of the device may be serrated with special orthopedic scissors to further facilitate the removal of the device. Once the device has been removed, the plaster dressing remains in place with all its edges applied absolutely correctly, substantially eliminating the possibility of any complications. Moreover, no matter how inexperienced the person applying the dressing may be, no application error can possibly be committed because the shape of the device precludes any technical error.

BRIEF DESCRIPTION OF THE DRAWINGS

FIG. 4 is a view, similar to FIG. 1, showing the dressing applied to the patient's forearm with the aid of the dressing devices in accordance with the invention;

FIG. 5 illustrates the manner in which the dressing devices are removed after the application of the dressing;

FIGS. 6 through 10 illustrate other applications of the device in accordance with the invention.

DESCRIPTION OF THE PREFERRED EMBODIMENTS

Figure 1:
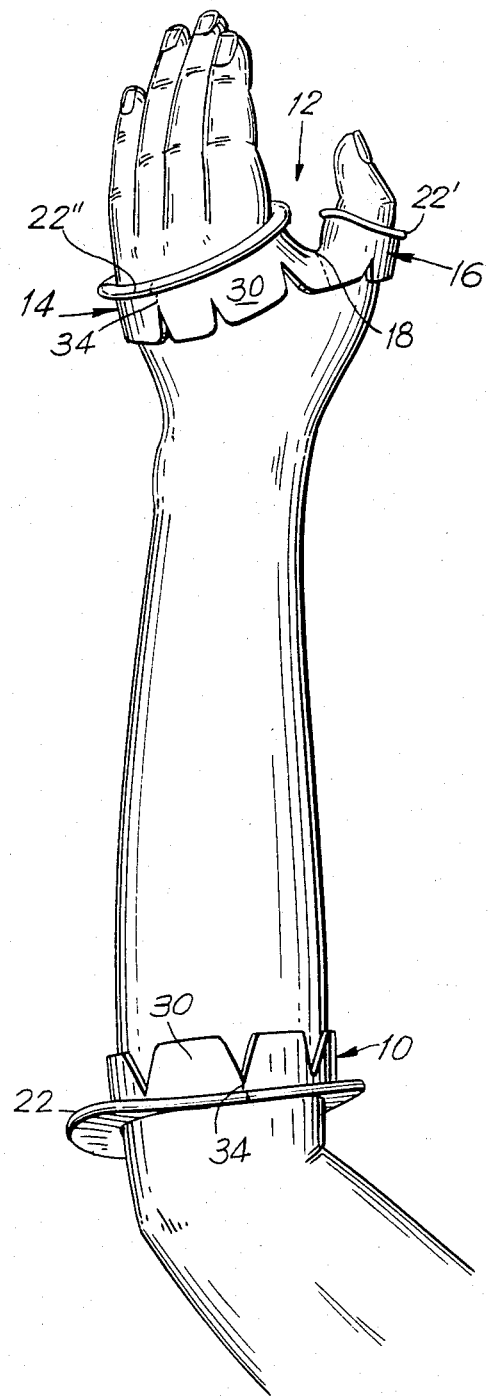
FIG. 1 is an elevational perspective view of a patient's forearm, provided with the correcting devices in accordance with the invention, for use in connection with a dressing to be applied where the patient has suffered a case of radius fracture.

Refering now to FIG. 1, there is shown the forearm and hand of a patient who has suffered a typical case of radius fracture requiring a plaster dressing applied to the wrist, wrist joint and forearm. In accordance with the invention, prior to the application of the plaster dressing, a dressing device 10 is placed about the forearm at a location corresponding to the intended location of the lower edge of the plaster dressing, and dressing device 12, comprising sections 14 and 16 interconnected by bridge 18, is placed about the hand and the thumb respectively.

Figure 2:
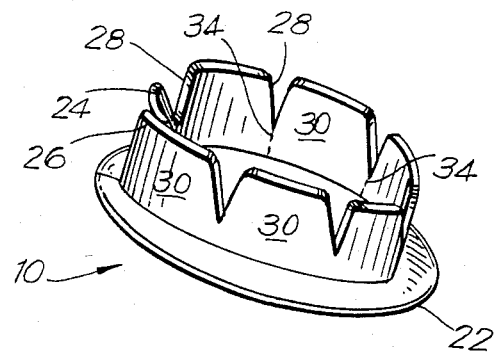

As best shown in FIG. 2, dressing device 10 comprises a split sleeve-like member having a skirt portion 20 depending from edge portion 22. Dressing device 10, which is made of any suitable plastic material, is resiliently formed into annular shape with the free ends 24 and 26 being in overlapping relation, the extent of overlap determining the size of the opening defined by the device. Edge portion 22 protrudes outwardly so as to define a limiting guide or stop for the plaster dressing to be applied over the dressing device. In order to make dressing device 10 more flexible and easier to remove, it is desirable to provide body portion 20 with cutouts 28 so as to form a plurality of side by side scallop shaped sections 30.

Due to the split nature and the resiliency of dressing device 10, it is a simple thing to place it about the patient's forearm as shown in FIG. 1. It will be understood that the smaller the forearm, the greater the overlap of free ends 24 and 26 and, conversely, the larger the forearm, the smaller the overlap. Conceivably, the forearm size could be large enough leaving no overlap, but defining instead, a small gap between the free ends.

Figure 3:
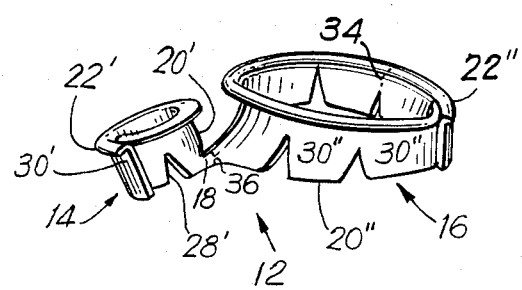
FIGS. 2 and 3 are elevational views of the two devices shown in FIG. 1.

Referring now to FIG. 3, there is shown dressing device 12 which comprises sections 14 and 16 interconnected by bridge 18. Sections 14 and 16 are substantially similar to device 10, each comprising outwardly protruding edge portions 22' and 22", respectively, from which depend skirt portions 20' and 20", respectively. As in the case of dressing device 10, dressing sections 14 and 16 are split so that they can easily be inserted about the appropriate body section and accommodate a range of sizes determined by the extent of overlap of the free ends. Also, as in the case of dressing device 10, skirt portions 20' and 20" are provided with cutouts 28' and 28", respectively, to define a plurality of side by side scallop shaped sections 30' and 30", respectively. Such construction, as previously stated, increases the flexibility of the dressing device and facilitates its removal after the plaster dressing has been applied.

With dressing devices 10, 12 and 14 in place, as shown in FIG. 1, it is a simple matter for the plaster dressing to be applied, even by someone not especially skilled in this area. As shown in FIG. 4, the plaster bandage dressing 32 is applied in conventional manner between edge portions 22', 22" on the hand and edge portion 22 on the forearm. These edges insure the proper application of the dressing whose upper and lower edges will be clearly and uniformly defined. In this connection, it will be noted that edge portions 22, 22' and 22" are outwardly turned to define a clear stop for the dressing thus positively locating the dressing where required and insuring the uniformity of the dressing's upper and lower extremities.

After the plaster sets, within 10 or 15 minutes, the disposable plastic dressing devices 10, 12 and 14 are removed by simply pulling them out by their outwardly turned edges, enabling the devices to smoothly exit from under the dressing without irritating the skin, as shown in FIG. 5. It will be apparent that the scalloped nature of the dressing device's skirt portions enables the dressing device to be easily withdrawn from under the dressing. To further facilitate the withdrawal of the dressing device, it may be perforated as at 34, between adjacent scalloped sections 30, so that these sections are easily separable from each other and thus more easily removable from under the dressing 32. It will also be evident that before dressing devices 12 and 14 can be removed, connecting bridge 18 must be cut and this too is facilitated by perforating the bridge as at 36. Once the dressing devices are all withdrawn, the dressing 32 remains in place, precisely as required, without any possibility of complications arising.

While the invention has been described in connection with a case of radius fracture, requiring a plaster dressing over the wrist, wrist joint and forearm, the invention is equally applicable where plaster dressings are required in connection with other medical conditions. In each situation, the particular shape of the dressing device will be determined by the body area involved. In each case, however, the dressing device will include a scalloped body or skirt portion extending from a peripheral outwardly protruding edge which will locate and define the outer limit of the dressing.

FIG. 6 illustrates a dressing device in position for applying a dressing in connection with a Bennett type fracture at the base of the thumb.

FIG. 7 illustrates a dressing device in position for applying a dressing in connection with fractures of the foot and ankle.

FIG. 8 illustrates a dressing device in position for applying a dressing for spica application in cases of hip or hip joint fractures.

FIG. 9 illustrates a dressing device in position for applying a dressing for application to the torso and an upper extremity.

FIG. 10 illustrates a dressing device in position for applying a dressing for application to the female torso.

While there is herein shown and described the preferred embodiments of the invention, it will be understood that the invention may be embodied otherwise than as herein specifically illustrated or described, and that in the illustrated embodiments certain changes in the details of construction and in the form and arrangement of parts may be made without departing from the underlying idea or principles of the invention within the scope of the appended claims.

Having thus described my invention, what I claim and desire to secure by letters patent is:

1. A device for correctly applying a plaster dressing to treat a fracture or dislocation of a human body segment comprising,
   (a) a split flexible plastic member normally urged into annular shape,
   (b) said member having an outwardly turned peripheral edge for its entire extent and a skirt portion depending therefrom, the depth of said skirt portion being substantially uniform for the entire extent thereof,
   (c) whereby said member is adapted to be placed on said body segment with said skirt portion in surrounding relation thereto and whereby said outwardly turned peripheral edge defines the limit of the plaster dressing,
   (d) said member being removable from under the plaster dressing after said dressing has been applied to said segment and has been set, and (e) said skirt portion being provided with cutouts so as to define a plurality of side by side scalloped sections for facilitating removal of said member from under the plaster dressing.

2. A device in accordance with claim 1, wherein perforations are provided between adjacent scalloped sections to enable said scalloped sections to be severed from each other in order to further facilitate removal of said member.

3. A device in accordance with claim 1, wherein the free ends of the split plastic member are in overlapping relation to define a closed annular member.

4. A device in accordance with claim 1, wherein the free ends of the split plastic member are spaced from each other to define a partially open annular member.

5. A method for correctly applying a plaster dressing to treat a fracture or dislocation of a human body segment comprising the steps of:
   (a) placing on said body segment a split flexible plastic member normally urged into annular shape, said member having an outwardly extending peripheral edge portion and a skirt portion depending therefrom which is in surrounding relation to said body segment.
   (b) applying a plurality of turns of plaster dressing about said skirt using said outwardly extending peripheral edge portion as a limiting guide for one of the dressing edges, and continuing to apply additional turns of plaster dressing beyond said skirt to cover the entire portion of the body segment requiring the plaster dressing, and
   (c) removing said flexible plastic member from under the plaster dressing after said plaster dressing has set, said skirt portion being provided with cutouts so as to define a plurality of side by side scalloped sections for facilitating said removing of said flexible plaster member from under said plaster dressing.

6. A method in accordance with claim 5, wherein perforations are provided between adjacent scalloped sections to enable said scalloped sections to be severed from each other in order to further facilitate removal of said member.

7. A method in accordance with claim 5, wherein the free ends of the split plastic member are in overlapping relation to define a closed annular member.

8. A method in accordance with claim 5, wherein the free ends of the split plastic member are spaced from each other to define a partially open annular member.

* * * * *